(12) United States Patent
Suddarth et al.

(10) Patent No.: US 12,226,438 B2
(45) Date of Patent: Feb. 18, 2025

(54) SYSTEM AND METHOD FOR THERAPEUTIC COMPOSITIONS FROM A PLURALITY OF DIFFERENT BIRTH TISSUES AND EXOSOMES

(71) Applicant: Hilltop BioSciences, Inc., Mansfield, MA (US)

(72) Inventors: Terrell Suddarth, New Market, AL (US); Amanda Drobnis, Norton, MA (US); Bruce Werber, Fort Lauderdale, FL (US); David Dutton, Comfort, TX (US)

(73) Assignee: Hilltop BioSciences, Inc., Mansfield, MA (US)

( * ) Notice: Subject to any disclaimer, the term of this patent is extended or adjusted under 35 U.S.C. 154(b) by 103 days.

(21) Appl. No.: 17/832,997

(22) Filed: Jun. 6, 2022

(65) Prior Publication Data

US 2022/0401496 A1    Dec. 22, 2022

Related U.S. Application Data (60) Provisional application No. 63/212,525, filed on Jun. 18, 2021.

(51) Int. Cl.
*A61K 35/50* (2015.01)
*A61K 35/51* (2015.01)

(52) U.S. Cl.
CPC .............. *A61K 35/50* (2013.01); *A61K 35/51* (2013.01)

(58) Field of Classification Search
CPC ................................ A61K 35/50; A61K 35/51
See application file for complete search history.

(56) References Cited

U.S. PATENT DOCUMENTS

| | | | |
|---|---|---|---|
| 10,835,558 B2 | 11/2020 | Brahm | |
| 11,026,980 B1 * | 6/2021 | Klitzke | A61L 26/0057 |
| 11,224,616 B1 | 1/2022 | Brahm | |
| 2003/0017150 A1 | 1/2003 | Torphy | |
| 2013/0211604 A1 | 8/2013 | Brundisini | |
| 2015/0010506 A1 * | 1/2015 | Jansen | A61K 38/1833 424/85.1 |
| 2019/0300848 A1 | 10/2019 | Fagg, IV et al. | |
| 2019/0307686 A1 * | 10/2019 | Ye | C12N 5/0636 |
| 2021/0036977 A1 | 12/2021 | Brahm | |
| 2022/0152120 A1 | 5/2022 | Qin et al. | |

FOREIGN PATENT DOCUMENTS

| | | |
|---|---|---|
| WO | WO 2008-036447 | 3/2008 |
| WO | WO 2013-082487 | 6/2013 |

OTHER PUBLICATIONS

Keelan, J.A. et al. "Cytokine abundance in placental tissues: Evidence of inflammatory activation in gestational membranes with term and preterm parturition" Am J Obstet Gynecol 1999, 181, 6, 1530-1536 (Year: 1999).*

Johnson, G.A. et al. "Osteopontin: Roles in Implantation and Placentation1" Biology of Reproduction 2003, 69, 1458-1471 (Year: 2003).*

PCT International Search Report for International Application PCT/US2022/011001, search report data of mailing Jul. 4, 2022 (Jul. 4, 2022).

* cited by examiner

*Primary Examiner* — Andrew S Rosenthal
(74) *Attorney, Agent, or Firm* — Daniel W. Roberts; Law Offices of Daniel W. Roberts, LLC (57) ABSTRACT

A method for a therapeutic compound from a plurality of birth tissues for the treatment of at least breathing and inflammation ailments. The method includes receiving a plurality of birth tissues from a mammalian donner. Each received birth tissue is processes to provide a refined material. This refined material is evaluated to determine at least a concentrate of at least one constituent. Portions of the processed birth tissues are then mixed to provide an initial blend of materials having a predetermined ration of the constituents to provide the therapeutic compound.

41 Claims, 5 Drawing Sheets

Airway patent protein concentration range
With final product containing the following proteins and concentration ranges:

| Protein | Low Concentration pg/mL | High Concentration pg/mL |
|---|---|---|
| IF-Ng | 180.0 | 1,300 |
| IL-1a | 0.5 | 300 |
| IL-1ra | 2,000.0 | 20,000 |
| IL-2 | 2.6 | 1,000 |
| IL-4 | 0.5 | 500 |
| IL-8 | 2.4 | 220 |
| IL-10 | 17.4 | 1,500 |
| IL-15 | 22.0 | 2,500 |
| MCP-1 | 2.6 | 500 |
| VEGF | 6.2 | 1,200 |

Extracellular vesicles ranging in size from 5nm to 220nm.

FIG. 5

SYSTEM AND METHOD FOR THERAPEUTIC COMPOSITIONS FROM A PLURALITY OF DIFFERENT BIRTH TISSUES AND EXOSOMES

CROSS REFERENCE TO RELATED APPLICATIONS

This application claims the benefit under 34 U.S.C. § 119(e) of U.S. Provisional Application No. 63/212,525 filed Jun. 18, 2021 and entitled SYSTEM AND METHOD FOR THERAPEUTIC COMPOSITIONS FROM A PLURALITY OF DIFFERENT BIRTH TISSUES, the disclosure of which is incorporated herein by reference.

FIELD OF THE INVENTION

The present invention relates generally to the processing and extraction of exosomes, cytokines, growth factors and associated proteins from mammalian birth tissues and creating compositions therefrom. More specifically this provides a processing technique to extract exosomes, cytokines, growth factors and associated proteins from mammals. This invention also provides for a process to make a compound or product for the treatment of mammalian aliments such as, but not limited to asthma, respiratory fibrosis, airway issues and associated modalities.

BACKGROUND

With a growing need to treat the devastating effects of chronic inflammatory diseases such as inflammatory airway disease, asthma, arthritis, joint inflammation, and other similar types of ailments in mammals, there is a growing need to provide an effective therapy that quickly reduces the inflammation and provides lasting relief from the effects of the inflammatory diseases.

Other diseases too, such as neutrophils, eosinophil, and other inflammatory response triggering disorders are also commonly problematic and in need of improved therapy and treatment options.

Mammalian birth tissue such as, but not exclusively limited to equine, canine, and feline amniotic fluid, Wharton's jelly and spongey layer between amnion and allantois or chorion, singularly or in any combination includes desirable attributes such as decreasing inflammation, decreasing fibrosis, increasing vascularization, improving healing, nerve regeneration, and reducing scar formation.

Mammalian birth tissue such as, but not exclusively limited to equine, canine, and feline amniotic fluid, Wharton's jelly and spongey layer between amnion and allantois or chorion, singularly or in any combination includes a rich source of growth and trophic factors, such as but not limited to exosomes, cytokines and other proteins whose activities are critical for coordinated development and modulation of healing.

Among the many types of inflammatory diseases, one example of an airway disease condition is Neutrophilic airway inflammation, a primary component seen in equine asthma, contributes to a propensity for airway constriction in response to normally innocuous stimuli (i.e., airway hyper-responsiveness), as well as airway remodeling in association with epithelial to mesenchymal transition. These structural changes include increases in goblet cells, airway smooth muscle, and fibrosis.

Moreover, with respect to many inflammatory diseases and/or inflammatory response triggering disorders such as allergies, there remains a wide spread need for improved treatment options such as precise compounds that are repeatedly producible so as to ensure consistent treatment based on known quantities of dosage.

Hence there is a need for an effective therapy that quickly reduces the inflammation and provides lasting relief from the effects of airway diseases, respiratory fibrosis and other airway issues.

SUMMARY OF THE INVENTION

Our invention solves the problems of the prior art by providing novel techniques to extract exosomes from multiple, different, mammalian birth tissues and combine them in varying formulations for the use in mammals, specifically equine, canine, and feline asthma, respiratory fibrosis, airway issues and associated modalities. These methods and compositions may also be applicable to human respiratory issues and ailments with the same or similar modalities of treatment.

In particular, and by way of example only, according to at least one embodiment, provided is a method for a therapeutic composition from a plurality of different birth tissues From at least one mammalian donor, including: receiving a first birth tissue; processing the first birth tissue to provide a first material; evaluating the first material to determine at least a first concentration of at least one first constituent; receiving a second birth tissue; processing the second birth tissue to provide a second material; evaluating the second material to determine at least a second concentration of at least one second constituent; and mixing at least a portion of the first material and at least a portion of the second material to provide an initial blend of materials having a predetermined ratio of the at least one first constituent and the at least one second constituent the initial blend of materials providing the therapeutic composition.

For yet another embodiment, provided is a method for a therapeutic composition from a plurality of different birth tissues, including: providing an amniotic fluid from a first mammalian donor; processing the amniotic fluid to provide first exosomes; providing umbilical cord material from a second mammalian donor; processing the umbilical cord material to harvest Warton's Jelly providing second exosomes; providing amnion and allantois material from between the amniotic layer and allantois membrane from a third mammalian donor; processing amnion and allantois material to provide third exosomes; and mixing at least a portion of the first exosomes, at least a portion of the second exosomes and at least a portion of the third exosomes to provide an initial blend of exosomes having a predetermined ratio of first exosomes, second exosomes and third exosomes; wherein the initial blend provides the therapeutic composition.

Still, for yet another embodiment, provided is a therapeutic composition from a plurality of different birth tissues including: a predetermined ratio of particles provided by at least processed first birth tissue providing at least one first constituent, processed second birth tissue providing at least one second constituent, and processed third birth tissue providing at least one third constituent, wherein the particles are about 30-250 nm; and a purified carrier fluid.

DETAILED DESCRIPTION

Before proceeding with the detailed description, it is to be appreciated that the present teaching is by way of example only, not by limitation. The concepts herein are not limited to use or application with a specific system or method for the collection and processing of mammalian birth tissues for producing advantageous compounds for the treatment of ailments. Thus, although the instrumentalities described herein are for the convenience of explanation shown and described with respect to exemplary embodiments, it will be understood and appreciated that the principles herein may be applied equally in other types of systems and methods involving the collection and processing of mammalian birth for producing advantageous compounds for the treatment of ailments.

This invention is described with respect to preferred embodiments in the following description with references to the Figures, in which like numbers represent the same or similar elements. It will be appreciated that the leading values identify the Figure in which the element is first identified and described, e.g., element 100 first appears in FIG. 1.

To briefly summarize, provided is a system, method and product that permits the extraction of exosomes, RNA, mRNA, growth factors and peptides for the preparation of therapeutic compositions. For at least one embodiment the prepared therapeutic composition is for treating mammalian airway diseases. Specifically, asthma, respiratory fibrosis, airway inflammation and associated modalities.

The invention also provides a composition comprising exosomes, RNA, mRNA, miRNA growth factors and peptides secreted by birth tissues, including but not limited to amnion, allantois, allantoamnion, umbilical cord, Wharton's jelly and amniotic fluid for promoting healing within the lung tissues.

As used herein, exosomes are understood and appreciated as membrane-bound extracellular vesicles that contain various molecular constituents of their cells of origin, including proteins, RNA, growth factors, etc. . . . . .

Moreover, as is further described below, the therapeutic compositions provided by embodiments of the present invention are derived through the combination of different materials derived from a plurality of different birth tissues. More specifically, although varying birth tissues may have similar elements, the concentrations of a given element may be greater or smaller for one birth tissue when compared with another birth tissue. Further, the processing of one birth tissue to derive a desired element may be easier or more efficient for one birth tissue than another.

In other words, by selectively blending processed elements from a plurality of different birth tissues in accordance with embodiments of the present invention, it is possible to prepare and provide specific therapeutic compositions with very specific ratios/blends of elements—and to do so repeatedly. Such precise repetition permits the advantageous production of essentially the same therapeutic composition again and again, or an alternative blending/mixing for a slightly different or entirely different therapeutic composition, which may also be repeated again and again.

At least some types of birth tissues may be understood and appreciated with respect to FIGS. 1A, 1B and 1C, FIG. 1 presents a conceptual illustration of an equine fetus 100 within the mother animal 102, aka the mammalian donor 102. More specifically the fetus 100 is developing within an amniotic sack 104. The amniotic sac 104 is essentially provided by a thin-walled membrane commonly referred to as the amnion 106 and an umbilical cord 108 interconnects the fetus 102 to the mother mammal 102. As may be appreciated in the enlarged section 110, there is fluid outside and around the amnion 106, most proximate to the mother, and amniotic fluid 112 within the amnion 106 most proximate to the fetus 100.

Figure 1A:
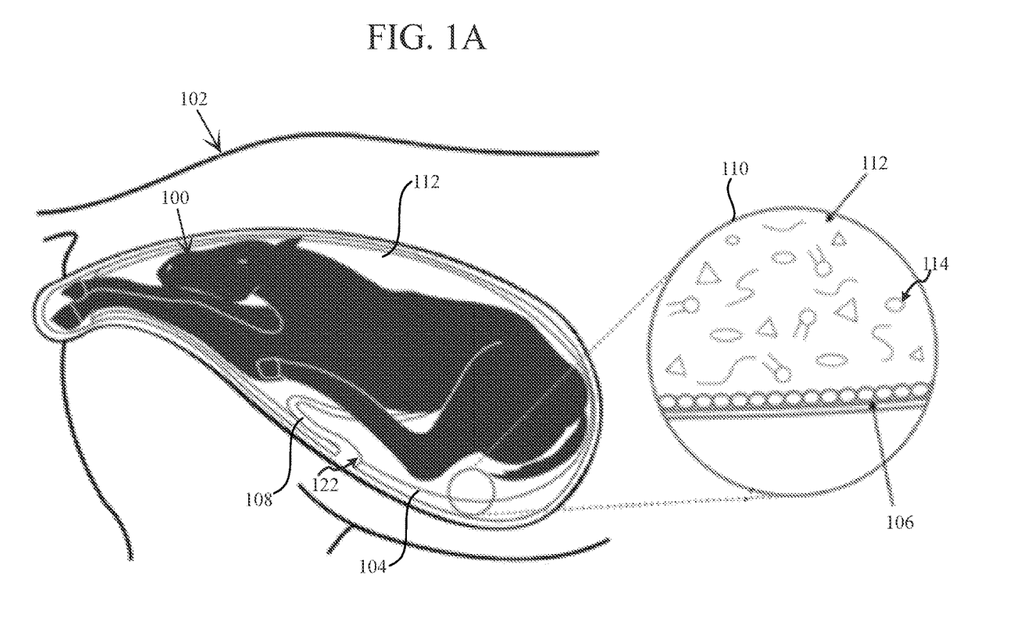
FIG. 1A is a conceptual illustration showing the locations of many birth tissues used to provide a therapeutic composition in accordance with at least one embodiment of the present invention.

As is also shown in the enlarged section 110, the amniotic fluid 112 has a plurality of exosomes, cytokines, growth factors (aka "GFS"), proteins, and other elements, collectively herein referred to as exosome suspension 114 within amniotic fluid 112. Although there may be some exosome suspension within the fluid proximate to the mother—e.g., outside of the amnion 106, it is most common for a far greater concentration of the exosome suspension 114 to be within the amniotic fluid 112 proximate to the fetus 100, thus within the amnion 106.

Figure 1B:
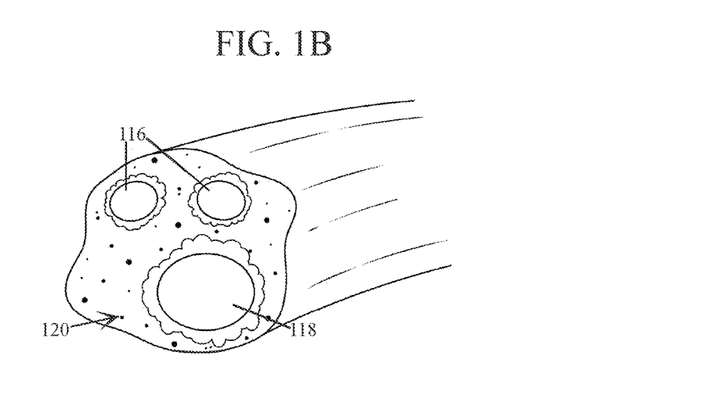
FIG. 1B is a perspective cross sectional view of a portion of an umbilical cord birth tissue showing the location of Wharton's jelly in accordance with at least one embodiment of the present invention.

FIG. 1B is an enlarged cross section of the umbilical cord 108 showing umbilical arteries 116 and an umbilical vein 118. The gelatinous material within the umbilical cord 108 that surrounds the umbilical arteries 116 and umbilical vein 118 is Wharton's jelly 120. Wharton's jelly 120 is generally comprised of mucopolysaccharides and acts as a mucous connective tissue that is rich in proteoglycans. Wharton's jelly 120 is also known to contain stem cells and stem cell genes, including telomerase.

It will be appreciated that there are three kinds of living mammals—eutherians, marsupials and monotremes, with the most obvious difference between them being the methods of reproduction. A more detailed discussion is not required, for the present invention is intended to be directed most commonly to eutherian mammals, also referred to as placental mammals.

Figure 1C:
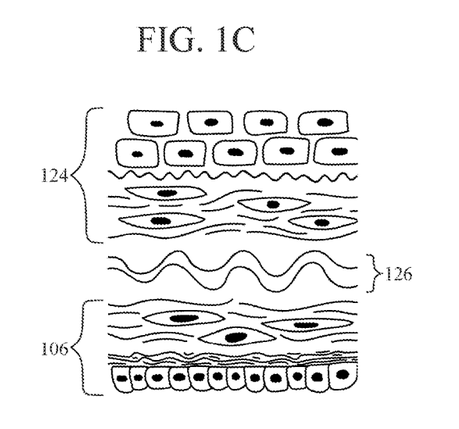
FIG. 1C is a cross section of placental region birth tissues showing the location of spongy layer birth tissue in accordance with at least one embodiment of the present invention.

FIG. 1C is an enlarged cross section from the placental area 122, showing the allantois 124 or chorion, amnion 106 and spongy layer 126, hereinafter simply referred to as the spongy layer 126.

Moreover, FIGS. 1A, 1B and 1C conceptualize the locations and original state of various birth tissues, including at least the amnion 106, the amnion sack 104, allantois 124, umbilical cord 108, and specific materials, such as, but not limited to, amniotic fluid 112, Wharton's jelly 120, and the spongy layer 126. For purposes of the present invention, it will be understood and appreciated that potential birth tissues for use in the further described advantageous therapeutic compositions and methods for their development include, but are not limited to, the amnion 106, allantois 124, allantoamnion, umbilical cord 108, Wharton's jelly 120, amniotic fluid 112, umbilical cord 108 blood, umbilical cord 108 blood extracts, and spongy layer 126.

Through testing and evolution of the resulting therapeutic compositions, it has been determined that the use of three different birth tissues for a given therapeutic composition provides consistent and repeatable qualities for a given therapeutic composition. However, it will be understood and appreciated that in some embodiments as few as two birth tissues may be used, or a plurality of more than three birth tissues may be used without departure from teachings herein provided.

Figure 2:
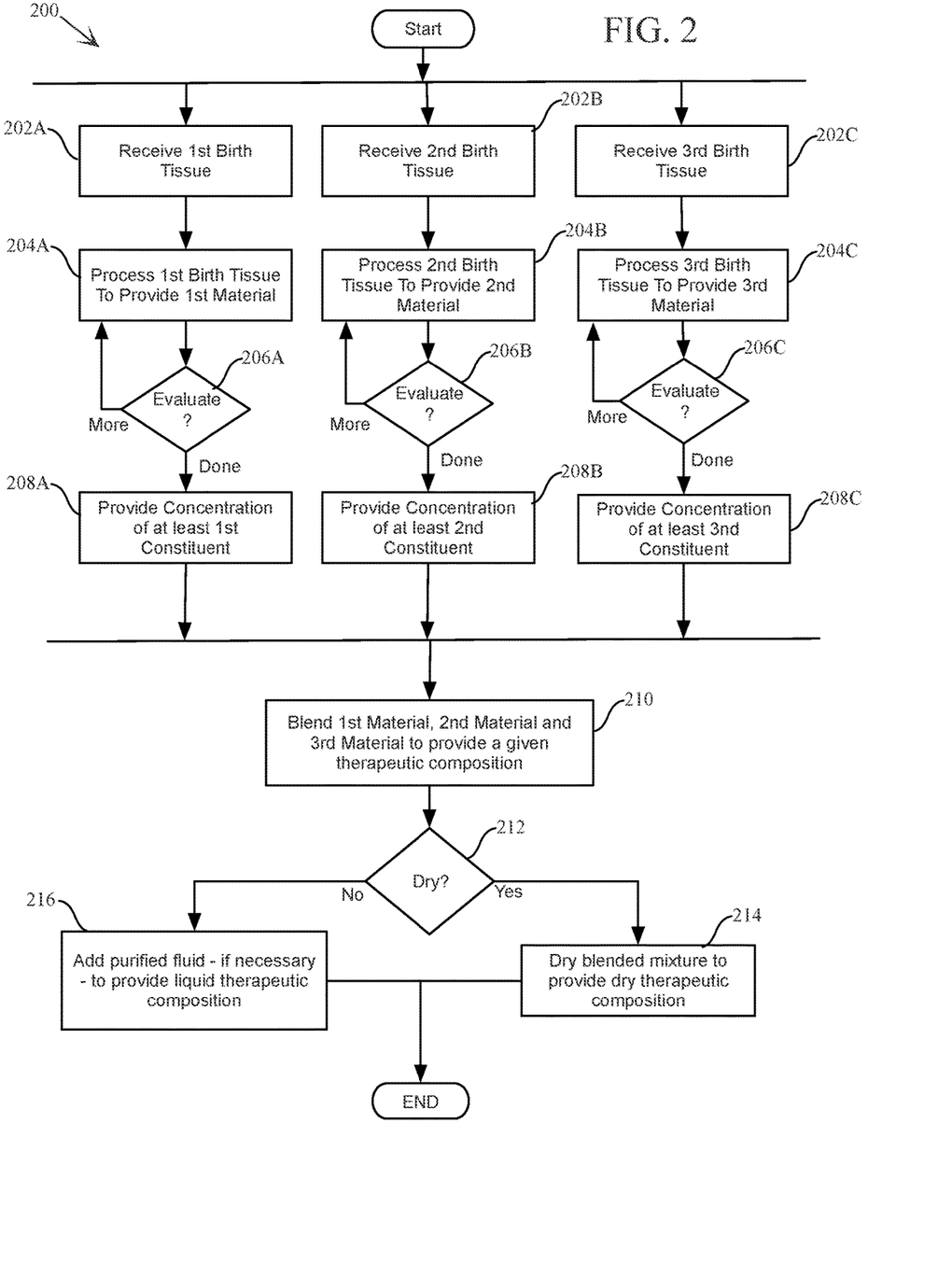
FIG. 2 is a flow diagram of a method of processing a plurality of birth tissues to provide a therapeutic composition in accordance with at least one embodiment of the present invention.
Figure 3:
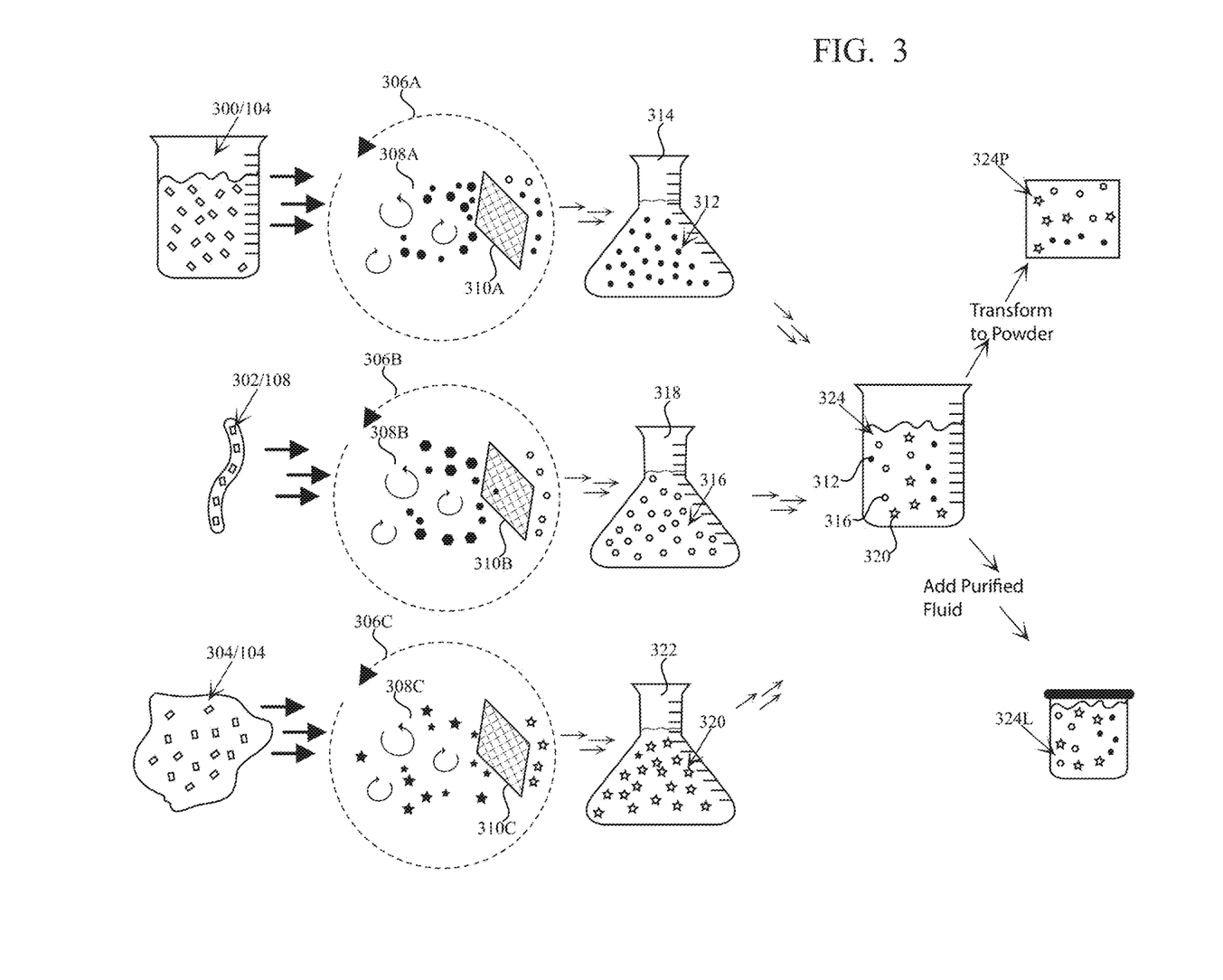
FIG. 3 is a conceptualization of the processing of the plurality of different birth tissues to provide a therapeutic composition in accordance with at least one embodiment of the present invention.

Turning now to FIGS. 2 and 3, presented are at least one method 200 for providing a therapeutic composition from a plurality of different birth tissues (see FIG. 2), and a conceptualization of the processing of various birth tissues to provide a therapeutic composition from a plurality of different birth tissues (see FIG. 3). As noted, the use of at least three birth tissues per given therapeutic composition are utilized in the following descriptions. It will also be understood and appreciated that the exemplary method 200 as set forth and herein described need not be performed in the described order of events, but that this order of description has been chosen for ease of illustration and description, and not intended as a limitation.

Moreover, method 200 and the process of providing a desired therapeutic composition commences with the collection of birth tissues. In general, the medical history, current charts, lab results and other data regarding the donor mother mammal is typically reviewed to determine and confirm suitability of mother for donation of the birth tissues. The collection process may be performed by the same parties who will subsequently process the birth tissues to provide the desired therapeutic compositions, or the collection may be performed by third parties.

For at least one embodiment, the collected birth tissues are placed in a −80 C ultra low temperature freezer for a period of at least 24 hours. This pre-chilling process begins to lyse any intact cells and free the desired exosomes. For yet another embodiment, the collected birth tissues are processed while still substantially fresh. For either option, as will be explained in greater detail below, desired exosomes are then captured from the birth tissues via dissection, filtration, manual extraction, centrifugation, magnetic bead extraction, SEC (size exclusion, molecular sieve, gel-filtration, gel permeation, chromatography), etc.

More specifically, as shown in FIG. 2, method 200 commences with the receiving of the birth tissues—receiving the first birth tissue, block 202A, receiving the second birth tissue, block 202B and receiving the third birth tissue, block 202C. In FIG. 3, the first birth tissue 300 is illustrated as a portion of amniotic fluid 112, the second birth tissue 302 is illustrated as a portion of the umbilical cord 108, and the third tissue 304 is illustrated as a portion of the amnion 104.

It will be understood and appreciated that for at least one embodiment, for processing, all necessary tissue components are thawed completely and then placed in a biological safety cabinet where a sterile field has been prepared.

With respect to the first birth tissue 300 as amniotic fluid 112, for at least one embodiment, the amniotic fluid 112 is processed and/or filtered through a series for progressively smaller pore size filters to remove any large debris. This processing and filtering may include ultra-centrifugation, mechanical filtration, magnetic bead processing, or any other means known to one skilled suitable for the processing and/or filtering of the amniotic fluid 112. For at least one embodiment, the fluid is further filtered through a 0.22 μm filter to capture a range of macro vesicles and exosomes with a variety of size ranges into an exosome suspension. This exosome suspension may be substantially as noted above—consisting of cytokines, growth factors (aka "GFS"), proteins, and other elements, but in contrast to the natural state of the amniotic fluid 112 as originally surrounding the fetus, this processed amniotic fluid 112 provides an exosome suspension wherein the exosome particulates have been filtered to remove other impurities and generally have a maximum size based on the level of filtration performed.

With respect to the processing and/or filtering of amniotic fluid 112, for at least one embodiment it will be understood and appreciated that such processing/filtering specifically does not de-cellulariz or acellularized the amniotic fluid 112. Moreover, the process/filtering specifically extracts the exosomes, RNA, mRNA, miRNA, growth factors, peptides and other proteins from the amniotic fluid. In other words, in contrast to systems and methods specifically seeking to de-cellulariz or acellulariz tissues or mammalian liquids into purified states with essentially no cellular or exosome properties, the present invention specifically teaches the refinements of tissues and fluids—specifically birth tissues and fluids, to derive high concentrations of known and desirable cellular materials and exosomes such as, but not limited to RNA, mRNA, miRNA, growth factors, peptides and other proteins, with these elements having known sizes as well as known concentrations.

With respect to the second birth tissue 302 as a portion of the umbilical cord 108, for at least one embodiment, a blunt needle and syringe containing isotonic solutions is used to flush the vein(s) and arteries of blood. Once the vessels are cleaned of blood, the section of cord is split using a scalpel blade longitudinally. Several cuts are made to cause the section of cord to lie flat. A cell lifter or similar instrument is used to scrape the cord section to remove the gelatinous, connective tissue (Wharton's Jelly 120 not shown). As this tissue is lifted from the cord section it is suspended in approximately 100 mL of amniotic fluid.

Regarding the second birth tissue 302 as a portion of the umbilical cord 108 being processed to retrieve Warton's Jelly 120 and/or cord blood, as well as the processing of the third birth tissue 304 as a portion of the amnion 104 to retrieve the spongey layer 126, it will be understood and appreciated that these successive processing steps are essentially recursive—the first birth tissue being processed to retrieve a more specific birth tissue—e.g., Wharton's Jelly 120 and the spongy layer 126, each of which is then further processed to extract desirable exosomes for subsequent recombination in the preparation of a therapeutic composition.

With respect to the third birth tissue 304 as a portion of the amnion 104, for at least one embodiment, the amnion 104 is separated from the allantois 124 using blunt dissection to expose the spongey material contained between the two layers. Each piece of tissue is laid flat on the work surface with the spongey material side of the tissue facing up. A cell lifter or similar instrument is used to scrap the spongey layer 126 contained between the amnion 106 and allantois 124. As the spongey layer 126 is lifted from the tissue layers, it is suspended in approximately 100 mL of amniotic fluid.

Moreover, the processing of a birth tissue as herein described is understood and appreciated to encompass successive processing actions such as scraping, grinding, fracturing, filtering, and the like so as to derive desired quantities of first, second and third materials from the first, second and third birth tissue components. The processing of each birth tissue may be performed contemporaneously as suggested by the parallel processing lines shown in FIG. 2, or as discrete actions occurring at different times. In addition, the processing phase may be a repetitive process where the tissues are ground, chopped, pulverized, or otherwise manipulated to extract elements of a specific size. These processing steps may of course involve repetitive filtering as is also illustrated.

More specifically, the processing step noted in FIG. 2 as blocks 204A, 204B and 204C, are shown as processing actions 306A, 306B and 306C wherein gears 308A, 308B and 308C and filters 310A, 310B and 310C are shown to represent the processing and filtering of each birth tissue so as to capture at least one or more distinct desired material, such as inherent proteins, growth factors, exosomes, cytokines, etc.

For the present example these desired materials are conceptualized as at least a first constituents 312 shown as solid dots in a first flask 314, at least a second constituents 316 shown as hexagons in a second flask 318, and at least a third constituents 320 shown as stars in a third flask 322. For at least one embodiment, such processing actions 306A, 306B and 306C are employed to derive at least one different constituent, or at least a different concentration of the constituent, from each birth tissue. Moreover, with some birth tissues, different constituents may be derived, and or derived in different concentrations. For yet other birth tissues, or even birth tissues from different donor mammals, similar constituents or even similar concentrations of constituents may be derived from different birth tissues from different donor mammals More specifically, different birth tissues may be selected and processed to derive specific exosomes as may be desired for one therapeutic composition of another.

For at least one embodiment, the method 200 includes evaluating each resulting materials—first constituents 312, second constituents 316 and third constituents 320—are evaluated to determine at least the concentration of the resulting constituents—see FIG. 2, decisions 206A, 206B, 206C. This evaluation may also include determining the particle size, and further processing may be performed if the concentrations, size or other factors are not yet as desired. The processing as indicated by blocks 204A, 204B and 204C continues until the evaluation of the at least one desired constituents is determined to be complete, blocks 208A, 208B and 208C.

With quantities of specifically desired constituents 308, 312 and 316 thus resulting from the processing, and as shown in the three different flasks 310, 314 and 318, one or more specific therapeutic compositions 324 may then be prepared by mixing the at least three different constituents 308, 312 and 316 in accordance with a developed formula to provide an initial blend of constituents having a predetermined ratio, block 210.

This therapeutic composition 324 is shown in FIG. 3 in flask 326, and to conceptualize the mixture of constituents is shown to have dots 312, circles 316 and stars 320 representing the various constituents derived from the processing of the various birth tissues. More specifically, therapeutic composition 324 provides known and pre-determined quantities and/or ratios of exosomes. As exosomes can transfer molecules from one cell to another via membrane vesicle trafficking, they can and do influence the immune system and advantageously appear to play a beneficial roll in mediating adaptive immune response to pathogens. As such, embodiments of the above methodology advantageously permit highly beneficial concentrations of exosomes to be derived from a plurality of birth tissues, such that specific therapeutic compounds may then be provided by mixing the concentrations of exosomes in accordance with various formulas to provide therapeutic compounds for specific ailments.

It should also be noted, that for ease of illustration and discussion, the conceptualized illustrations and above discussion have focused upon deriving at least three different constituents 308, 312 and 316 from the initial birth tissues. And yes, indeed it will be understood and appreciated that each birth tissue may indeed be processed to derive at least one specific constituent. However, it will be understood and appreciated, that the disclosed method and processing techniques are not necessarily intended to provide different constituents in isolation of other materials. Rather, it will be understood and appreciated that in addition to the desired and different constituents—e.g., specific exosomes, in general the employed embodiments of the present invention will also yield the harvesting of free-floating growth factors, cytokines, other proteins and the like. These additional elements are beneficial and desirable and understood to more than likely to be harvested in addition to the different constituents, but unless they are deemed to be the intended constituents, are not necessarily specifically tested for or evaluated for specific concentration.

This process may be summarized as a method for a therapeutic composition 324 from a plurality of different birth tissues from at least one mammalian donor 102, including: receiving a first birth tissue 300; processing the first birth tissue 300 to provide a first material; evaluating the first material to determine at least a first concentration of at least one first constituent 312; receiving a second birth tissue 302; processing the second birth tissue 302 to provide a second material; evaluating the second material to determine at least a second concentration of at least one second constituent 316; and mixing at least a portion of the first material and at least a portion of the second material to provide an initial blend of materials having a predetermined ratio of the at least one first constituent 312 and the at least one second constituent 316 the initial blend of materials providing the therapeutic composition 324.

Further still, the first constituents, second constituents and third constituents may also be recognized as exosomes, accordingly first exosomes, second exosomes and third exosomes. Moreover, according to at least one embodiment, the method or process may be summarized as a method for a therapeutic composition 324 from a plurality of different birth tissues; including: providing an amniotic fluid 112 from a first mammalian donor; processing the amniotic fluid 112 to provide first exosomes; providing umbilical cord 108 material from a second mammalian donor; processing the umbilical cord 108 material to harvest Wanton's Jelly 120 providing second exosomes; providing amnion 106 and allantois 124 material from between the amniotic layer and allantois 124 membrane from a third mammalian donor; processing amnion 106 and allantois 124 material to provide third exosomes; and mixing at least a portion of the first exosomes, at least a portion of the second exosomes and at least a portion of the third exosomes to provide an initial blend of exosomes having a predetermined ratio of first exosomes, second exosomes and third exosomes; wherein the initial blend provides the therapeutic composition 324.

As indicated by decision 212, this therapeutic composition 324 may be further processed such as by lyophilizing (freezing-drying) to a residual moisture content of about 6% or less to provide an essentially dry or powered therapeutic composition 324P, shown as block 214 in method 200, for transport or storage. The therapeutic composition 324 may also be processed by adding a sterile liquid (if necessary) to provide a liquid therapeutic composition 324L then packaging in sealed bottles for transport or storage, shown as block 216 in method 200.

In another embodiment, pH adjustments may be made to the exosome suspension by adding a sodium phosphate solution per 100 mL of suspension. For lyophilized preservation, sucrose may be added per 100 mL to aid in the lyophilization process. More specifically, for at least one embodiment, the pH adjustments are achieved with the following methodology: 6% sucrose and 5 mM Phosphate (pH 7.2)=40 mL=2.4 g Sucrose, Sodium Phosphate Dibasic 20.6 milligrams, Sodium phosphate monobasic 6.72 milligrams.

Dilution and/or concentration calculations are made using the size/number of captured exosomes to estimate the number of vials that can be filled at a given volume.

More specifically, the at least one embodiment of a method shown and described with respect to FIG. 3 provides a therapeutic composition 324 including a predetermined ratio of particles provided by at least processed first birth tissue 324 providing at least one first constituent 312, processed second birth tissue 302 providing at least one second constituent 316, and processed third birth tissue 304 providing at least one third constituent 320, wherein the particles are about 30-250 nm; and a purified carrier fluid.

Dilution or concentration of the exosome suspension is performed depending on the number of exosomes collected. Aliquots of the desired suspension volume are deposited into sterile cryogenic and/or serum vials within the sterile field. Vials may be placed into a refrigerator for initial cooling. Within 24 hours the vials are then placed into an ultra-low freezer for storage.

Specific to a frozen technique dilution and/or concentration of the exosome suspension is carried out and aliquots of the desired suspension volume are deposited in sterile cryovials vials within the sterile field. The suspension is aspirated/expressed using a pipette at regular intervals during the filling process to maintain homogeneity. The filled cryovials are capped, placed in vial racks and passed to the circulator who labels each individual vial with a unit number, then immediately transfers the units into the laboratory refrigerator. Once all vials have been labelled and placed in lab refrigerator, the vial racks are moved to an ultra-low temp freezer for initial freezing. Once initial freezing is complete, the vials are moved to bulk vial storage boxes in the quarantine section of the ultra-low temperature freezer where they remain until Quality release for final packaging and shipment.

Moreover, in at least one embodiment the invention is provided in the form of a lyophilized solution for the purposes of treating mammalian airway diseases via nebulization, intravenous, intramuscular, or other modalities already known.

Specific to a lyophilized technique dilution and/or concentration of the exosome suspension is carried out along with the addition of proprietary stabilizing components. Aliquots of the desired suspension volume are deposited in sterile serum vials within the sterile field. The suspension is aspirated/expressed using a pipette at regular intervals during the filling process to maintain homogeneity. Lyophilization stoppers are inserted to the first vent ridge into the filled serum vials, placed in vial racks, and racks sealed in lyophilization pouches then passed to the circulator who transfers the units into the laboratory refrigerator. Once all vials have been stoppered and placed in lab refrigerator, the vial racks are moved to the lyophilizer for processing. Once lyophilization is complete, the vials are fully stoppered, crimp capped, labeled and moved to the quarantine section of QC WIP where they remain until Quality release for final packaging and shipment.

In one embodiment, lyophilization occurs to a maximum of 6% residual moisture, however it will be understood and appreciated that in many cases the residual moisture may actually be <1%.

Figure 4:
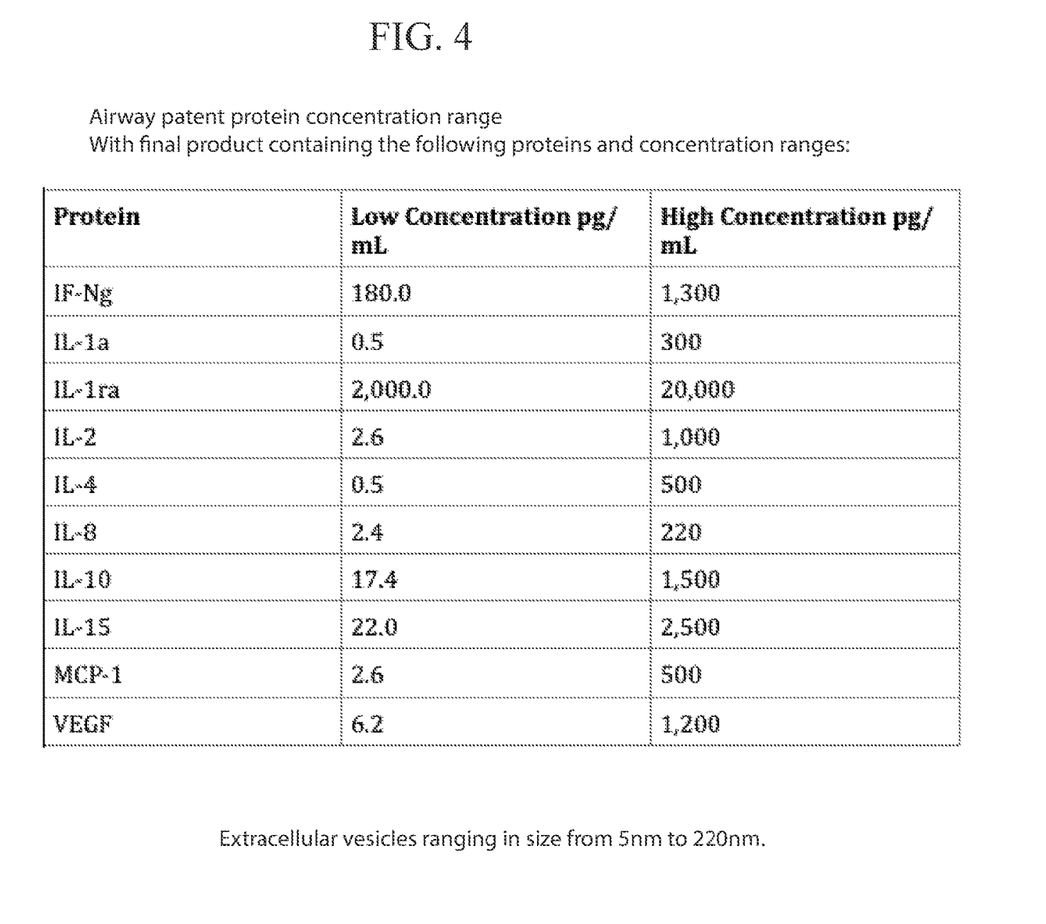
FIG. 4 is a chart listing known components that have been identified to play a key role in the mechanisms of biological healing achieved by at least one therapeutic composition in accordance with at least one embodiment of the present invention.

In another embodiment final products from both frozen and lyophilized products contain exosomes in the range of 30-250 nm. These exosomes will have variable cargo of miRNA, messenger RNA, growth factors, cytokines and peptides. FIG. 4 presents a table of constituents, e.g., proteins, that have been derived from performing the present invention.

In one embodiment the final products from both frozen and lyophilized processing contain total proteins in the range of 0.05-1.681 mg/mL.

Figure 5:
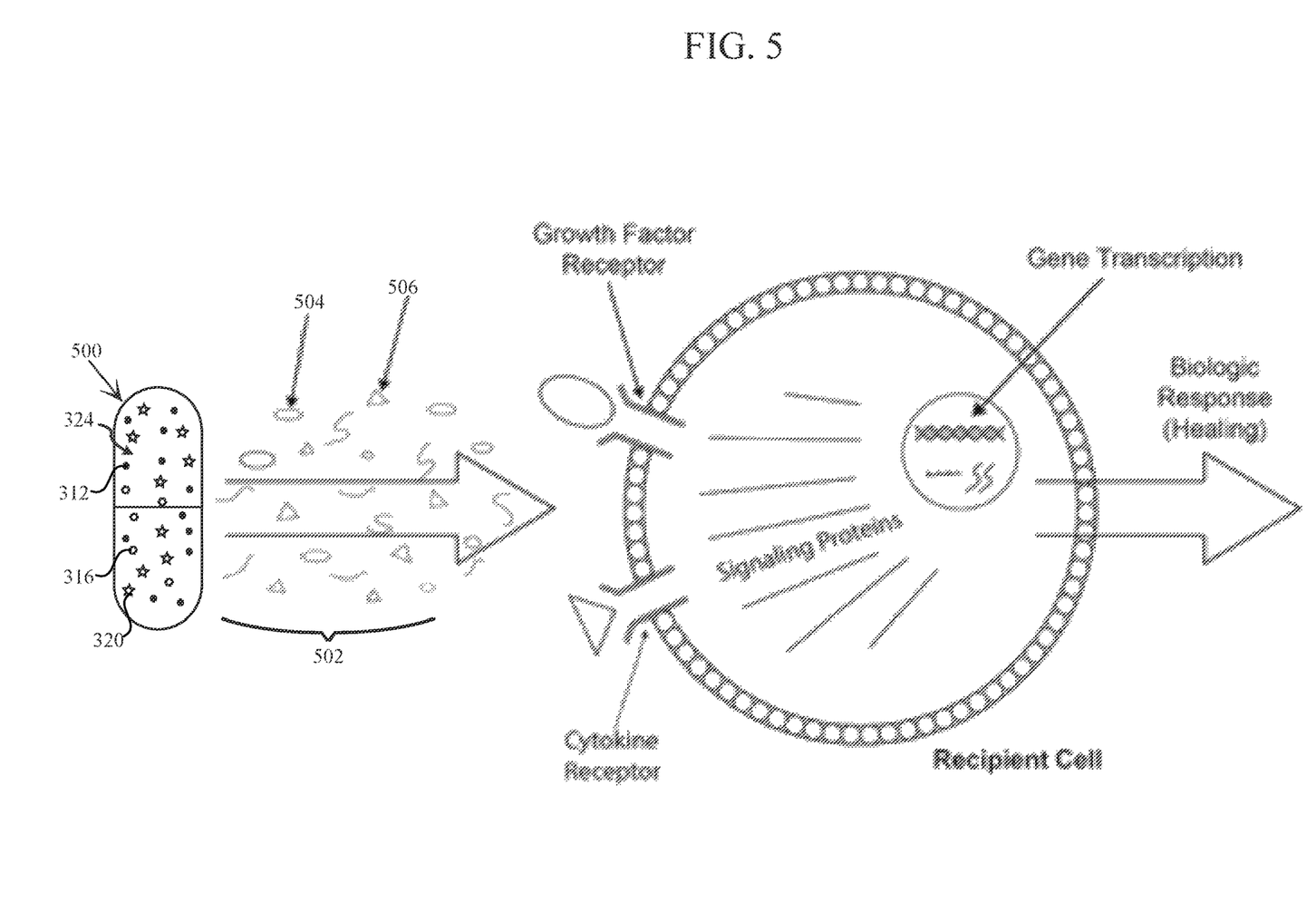
FIG. 5 is a conceptualization of at least one therapeutic composition being applied to a patient animal to induce healing in accordance with at least one embodiment of the present invention.

FIG. 5 is a conceptual illustration of a therapeutic composition 324 being applied as a dosage 500 to a patient animal, conceptualized at a quazi-cellular level. As noted above, the exosomes extracted from the processed birth tissues have been combined in various ways for the treatment of specific ailments. As these exosomes can transfer molecules from cell to another via membrane vesicle trafficking, the specifically derived therapeutic composition 324 is advantageously desirable as it permits the delivery of proteins, RNA, mRNA, miRNA, growth factors and other elements directly to cells for the treatment of various ailments.

More specifically, dosage 500 delivers the therapeutic composition 324 into the bloodstream of the patient animal requiring treatment. The therapeutic composition 324 has been formulated to provide a specific exosome suspension 502, providing growth factors, proteins, cytokines, and or such other materials as have been determined most appropriate for the treatment of the ailment at issue. The exosome suspension 502 is in turn picked up by various cells in the patient animal, wherein the exosome suspension 502 triggers the development of proteins and/or other processes which aid in biologic healing of the patient animal.

In another embodiment, the birth tissues comprise lymphocytes, monocytes, neutrophils, eosinophils, and/or basophils singularly or in any combination.

In one embodiment, the composition is administered in a single application.

In another embodiment, the composition is administered periodically.

In another embodiment, the composition is administered once daily.

In another embodiment, this therapeutic composition is delivered via nebulization, lavage, intravenous, intramuscular or any other commercially available device.

In another embodiment, the final lyophilized products are delivered with a mixture of sterile saline, lactated ringers, phosphate buffered saline, or other readily available mixture.

In yet another embodiment, the preferred equine birth tissues include amnion, allantois, allantoamnion, umbilical cord, Wharton's jelly, amniotic fluid, umbilical cord blood, umbilical cord blood extracts, spongey layer and related tissues.

In another embodiment, the preferred canine and feline birth tissues include amnion, chorioallantois, umbilical cord, Wharton's jelly, amniotic fluid and related tissues.

In another embodiment, this technique uses human birth tissues including amnion, amniotic fluid, umbilical cord, umbilical cord blood extracts, Wharton's jelly, spongey layer and other related tissues.

With respect to providing a therapeutic composition, it is understood and appreciated that at least one advantage of the present invention is the advantageous ability to ensure consistency with the production of various therapeutic compositions. This formulation is based on a desired range of proteins to be contained in each aliquot and is determined by the size and number of exosomes captured from the birth tissue components.

More specifically, with respect to the above description and the resulting proteins derived from the plurality of birth tissues, for at least one embodiment the derived proteins are selected from the group consisting of—but not exclusively limited to: IF-Ng, IL-1a, IL-1ra, IL-2, IL-4, IL-8, IL-8, IL-10, IL-15, MCP-1, EGF, VEGF, Osteopontin, Epidermal GF, Extracellular Matrix Protein 1.

With respect to this list of derived proteins, those skilled in the part will appreciate that the "IL-" values refer to specific cytokines that have pleiotropic: functions in inflammation and cancer, the IL-# referring to the specific gene encoding the protein. MCP-1 is Monocyte Chemoattractant Protein-1 is a member of the chemoattractant cytokine family and are known to regulate the migration and infiltration of monocytes/macrophages. EGF refers to Endothelial Growth Factor and VEGF refers to Vascular Endothelial Growth Factor, and IF-Ng is a Type II interferon produced by immune cells such as T-cells and NK cells, and is known to play a curtail roll in antimicrobial, antiviral and antitumor responses by activating effector immune cells and enhancing antigen presentation.

Moreover, the above describe processing and refinement methodology as applied to the plurality of mammalian birth tissues advantageously permits the collection of at least these known and specific proteins which have been identified and are appreciated to mitigate and promote recovery from at least inflammation and respiratory ailments. Outside of birth tissues, these protein elements are often rare, so the advantageous ability to extract them and concentrate their collection from birth tissues, provides an advantageous opportunity for preparing a variety of advantageous therapeutic compounds for the treatment of at least breathing and inflammation ailments.

For at least one embodiment, the formula used for a therapeutic composition for the treatment of mammalian airway diseases and/or inflammation is:

$$1 \text{ mL} = a(\text{Osteopontin}) + b(\text{Epidermal GF}) + c(\text{Extracellular Matrix Protein1}) \quad \text{Formula \#1}$$

Where a, b, and c are variables with the following ranges, for each of the proteins identified within the brackets "( . . . )":

| Variable | Low | | High | |
| --- | --- | --- | --- | --- |
| a | 34.51 | ng/mL | 182.65 | ng/mL |
| b | 128.45 | pg/mL | 643.78 | pg/mL |
| c | 56.16 | pg/mL | 443.21 | pg/mL |

In other words, Formula #1 provides 1 mL of a therapeutic composition comprised by the protein Osteopontin in a range of between about 34.51 ng/ml to about 182.65 ng/ml, the protein Epidermal GF in a range of between about 128.45 pg/ml to about 643.78 pg/ml, and the protein Extracellular Matrix Protein in a range of between about 56.16 pg/ml to about 443.21 pg/ml.

For at least another one embodiment, the formula used for a therapeutic composition for the treatment of mammalian airway diseases and/or inflammation is:

$$1 \text{ mL} = u(\text{IL-1}a) + v(\text{IL-1}ra) + w(\text{IL-8}) + x(\text{IL-10}) + y(\text{MCP-1}) + z(\text{VEGF}) \quad \text{Formula \#2}$$

Where u, v, w, x, y, and z are variables with the following ranges, for each of the proteins identified within the brackets "( . . . )":

| Variable | Low | | High | |
| --- | --- | --- | --- | --- |
| u | 7.6991 | pg/mL | 53.8151 | pg/mL |
| v | 0.8401 | pg/mL | 26,617.7701 | pg/mL |
| w | 62.6565 | pg/mL | 263.2149 | pg/mL |
| x | 0.0145 | pg/mL | 88.5287 | pg/mL |
| y | 293.824 | pg/mL | 696.8044 | pg/mL |
| z | 385.9375 | pg/mL | 1,059.7339 | pg/mL |

In other words, Formula #2 provides 1 mL of a therapeutic composition comprised by protein IL-1a in a range of between about 7.6991 pg/ml to about 53.8151 pg/ml, the protein IL-1ra in a range of between about 0.8401 pg/ml to about 26,617.7701 pg/ml, the protein IL-8 in a range of between about 62.6565 pg/ml to about 263.2149 pg/ml, the protein IL-10 in a range of between about 0.0145 pg/ml to about 88.5287 pg/ml, the protein MCP-1 in a range of between about 293.824 pg/ml to about 696.8044 pg/ml, and the protein VEGF in a range of between about 385.9375 pg/ml to about 1,059.7339 pg/ml.

For this embodiment, the resulting therapeutic composition has the following properties: $1 \text{ mL} = 0.95\text{-}4.85 \times 10^{11}$ exosomes ranging in size from 30 nm to 250 nm.

In this embodiment, 1EU=x % IF-Ng+x % IL-1a+x % IL-1ra+x % IL-2+x % IL-4+x % IL-8+x % IL-8+x % IL-10+x % IL-15+x % MCP-1+x % EGF+x %+x % VEGF where x varies from 0% to 100% to make the final product for the treatment of mammalian airway diseases.

In another embodiment the formula used for the treatment of mammalian airway diseases includes 100±5 mL of amniotic fluid, Wharton's jelly from a 4±1 cm Umbilical cord section and 200±20 cm² of spongey layer between the amnion/allantois.

Moreover, Formula #1 presents a therapeutic composition comprised essentially of three constituents/exosomes (e.g., Osteopontin, Epidermal Growth Factor, and Extracellular Matrix Protein 1) derived by an embodiment of the present invention as discussed and described above with respect to the processing of at two or more discreet birth tissues. Formula #2 extends on the advantage of at least three constituents/exosomes, by incorporating six constituents/exosomes (e.g., IL-1a, IL-1ra, IL-8, IL-10, y(MCP-1, and VEGF) derived by an embodiment of the present invention as discussed and described above with respect to the processing of at two or more discreet birth tissues.

Changes may be made in the above methods, systems and structures without departing from the scope hereof. It should thus be noted that the matter contained in the above description and/or shown in the accompanying drawings should be interpreted as illustrative and not in a limiting sense. Indeed, many other embodiments are feasible and possible, as will be evident to one of ordinary skill in the art. The claims that follow are not limited by or to the embodiments discussed herein, but are limited solely by their terms and the Doctrine of Equivalents.

What is claimed:

1. A method for making a therapeutic composition from a plurality of different birth tissues from at least one mammalian donor, comprising:
   receiving a first birth tissue;
   processing the first birth tissue to isolate first subcellular elements from the first birth tissue;
   evaluating the isolated first subcellular elements to determine at least a first concentration of at least one first constituent;
   receiving a second birth tissue;
   processing the second birth tissue to isolate second subcellular elements;
   evaluating the isolated second subcellular elements to determine at least a second concentration of at least one second constituent; and
   mixing at least a portion of the isolated first subcellular elements and at least a portion of the isolated second subcellular elements to provide an initial blend of isolated subcellular elements having a predetermined ratio of the at least one first constituent and the at least one second constituent in the initial blend of isolated subcellular elements providing the therapeutic composition;
   wherein each birth tissue is different and selected from the group consisting of: amnion, allantois, allantoamnion, umbilical cord, Wharton's jelly, amniotic fluid, umbilical cord blood, umbilical cord blood extracts, and spongey layer.

2. The method of claim 1, further including at least one additional birth tissue, comprising:
   receiving a third birth tissue;
   processing the third birth tissue to isolate third subcellular elements;
   evaluating the isolated third subcellular elements to determine at least a third concentration of at least one third constituent; and
   mixing at least a portion of the isolated third subcellular elements with the portion of the isolated first subcellular elements and the portion of the isolated second subcellular elements to provide the therapeutic composition.

3. The method of claim 1, further including adding the initial blend of isolated subcellular elements to a purified fluid to provide the therapeutic composition.

4. The method of claim 1, wherein each constituent is selected from the group consisting essentially of: proteins, growth factors, exosomes, cytokines, lipids, RNS, mRNA, miRNA, RNS, and DNA.

5. The method of claim 1, wherein each constituent is selected from the group of proteins consisting essentially of: IF-Ng, IL-1a, IL-1ra, IL-2, IL-4, IL-8, IL-8, IL-10, IL-15, MCP-1, EGF, and VEGF.

6. The method of claim 1, wherein each constituent is selected from the group of proteins consisting essentially of: Osteopontin, Epidermal Growth Factor, and Extracellular Matrix Protein 1.

7. The method of claim 1, further including cryopreserving the therapeutic composition to produce a cryopreserved therapeutic composition.

8. The method of claim 1, wherein the processing each birth tissue provides isolated subcellular elements having constituents of about 30-250 nm.

9. The method of claim 1, wherein the birth tissues are from the same mammalian donor.

10. The method of claim 1, wherein the birth tissues are from at least two different mammalian donors.

11. The method of claim 1, wherein at least one mammalian is equine.

12. The method of claim 1, wherein at least one mammalian is feline.

13. The method of claim 1, wherein at least one mammalian is human.

14. The method of claim 1, wherein at least one mammalian is canine.

15. The method of claim 1, wherein the therapeutic composition is for the treatment of breathing disorders.

16. The method of claim 1, wherein the therapeutic composition is for the treatment of inflammation disorders.

17. A method for making a therapeutic composition from a plurality of different birth tissues, comprising:
   providing an amniotic fluid from a first mammalian donor;
   processing the amniotic fluid to provide first exosomes;
   providing umbilical cord material from a second mammalian donor;
   processing the umbilical cord material to harvest Wharton's Jelly providing second exosomes;
   providing amnion and allantois material from between the amniotic layer and allantois membrane from a third mammalian donor;
   processing amnion and allantois material to provide third exosomes; and
   mixing at least a portion of the first exosomes, at least a portion of the second exosomes and at least a portion of the third exosomes to provide an initial blend of exosomes having a predetermined ratio of first exosomes, second exosomes and third exosomes;
   wherein the initial blend provides the therapeutic composition.

18. The method of claim 17, further including adding the initial blend of exosomes to a purified fluid to provide the therapeutic composition.

19. The method of claim 17, wherein the amnion and allantois processing includes scraping a spongey cellular material from between the amnion and allantois.

20. The method of claim 17, wherein the amniotic fluid is filtered through at least a 0.22 μm filter.

21. The method of claim 17, wherein the at least one first exosomes, the at least one second exosomes, and the at least one third exosomes are selected from the group consisting essentially of: proteins, growth factors, exosomes, cytokines, lipids, RNA, mRNA, miRNA, RNS, and DNA.

22. The method of claim 17, wherein the at least one first exosomes, the at least one second exosomes, and the at least one third exosomes are selected from the group of proteins consisting essentially of: IF-Ng, IL-1a, IL-1ra, IL-2, IL-4, IL-8, IL-8, IL-10, IL-15, MCP-1, EGF, and VEGF.

23. The method of claim 17, wherein the at least one first exosomes, the at least one second exosomes, and the at least one third exosomes are selected from the group of proteins consisting essentially of: Osteopontin, Epidermal Growth Factor, and Extracellular Matrix Protein 1.

24. The method of claim 17, further including cryopreserving the therapeutic composition to produce a cryopreserved therapeutic composition.

25. The method of claim 17, further including lyophilizing the therapeutic composition to produce a freeze-dried therapeutic composition.

26. The method of claim 17, wherein the processing of the amniotic fluid provides first exosomes of about 30-250 nm.

27. The method of claim 17, wherein the processing of the umbilical cord material provides second exosomes of about 30-250 nm.

28. The method of claim 17, wherein the processing of the amnion and allantois provides third exosomes of about 30-250 nm.

29. The method of claim 17, wherein the first mammalian donor, the second mammalian donor, and the third mammalian donor are the same mammalian donor.

30. The method of claim 17, wherein at least two of the first mammalian donor, the second mammalian donor, and the third mammalian donor are different donors.

31. The method of claim 17, wherein the therapeutic composition is for the treatment of breathing disorders.

32. The method of claim 17, wherein the therapeutic composition is for the treatment of inflammation disorders.

33. A method for making a therapeutic composition from a plurality of different birth tissues from at least one mammalian donor, comprising:
   receiving a first birth tissue;
   processing the first birth tissue to isolate first subcellular elements;
   evaluating the isolated first subcellular elements to determine at least a first concentration of at least one first constituent;
   receiving a second birth tissue;
   processing the second birth tissue to isolate second subcellular elements;
   evaluating the isolated second subcellular elements to determine at least a second concentration of at least one second constituent; and
   mixing at least a portion of the isolated first material and at least a portion of the isolated second material to provide an initial blend of isolated subcellular elements having a predetermined ratio of the at least one first constituent and the at least one second constituent in the initial blend of isolated subcellular elements providing the therapeutic composition, each constituent selected from the group consisting essentially of: proteins, growth factors, exosomes, cytokines, lipids, RNS, mRNA, miRNA, RNS, and DNA;
   wherein each birth tissue is different and selected from the group consisting of: amnion, allantois, allantoamnion, umbilical cord, Wharton's jelly, amniotic fluid, umbilical cord blood, umbilical cord blood extracts, and spongey layer.

34. The method of claim 33, further including at least one additional birth tissue, comprising:
   receiving a third birth tissue;
   processing the third birth tissue to isolate third subcellular elements;
   evaluating the isolated third subcellular elements to determine at least a third concentration of at least one third constituent; and
   mixing at least a portion of the third subcellular elements with the portion of the isolated first subcellular elements and the portion of the isolated second subcellular elements to provide the therapeutic composition.

35. The method of claim 33, further including adding the initial blend of isolated subcellular elements to a purified fluid to provide the therapeutic composition.

36. The method of claim 33, wherein each constituent is selected from the group consisting essentially of: proteins, growth factors, exosomes, cytokines, lipids, RNS, mRNA, miRNA, RNS, and DNA.

37. The method of claim 33, wherein each constituent is selected from the group of proteins consisting essentially of: IF-Ng, IL-1a, IL-1ra, IL-2, IL-4, IL-8, IL-8, IL-10, IL-15, MCP-1, EGF, and VEGF.

38. The method of claim 33, wherein each constituent is selected from the group of proteins consisting essentially of: Osteopontin, Epidermal Growth Factor, and Extracellular Matrix Protein 1.

39. The method of claim 33, wherein the processing each birth tissue provides isolated subcellular elements having constituents of about 30-250 nm.

40. The method of claim 33, wherein the therapeutic composition is for the treatment of breathing disorders.

41. The method of claim 33, wherein the therapeutic composition is for the treatment of inflammation disorders.

* * * * *